(12) United States Patent
Kang et al.

(10) Patent No.: US 9,872,692 B2
(45) Date of Patent: Jan. 23, 2018

(54) MOTION-COMPENSATED MICRO-FORCEPS SYSTEM AND METHOD

(71) Applicant: The Johns Hopkins University, Baltimore, MD (US)

(72) Inventors: Jin U. Kang, Ellicott City, MD (US); Peter L. Gehlbach, Monkton, MD (US)

(73) Assignee: The Johns Hopkins University, Baltimore, MD (US)

( * ) Notice: Subject to any disclaimer, the term of this patent is extended or adjusted under 35 U.S.C. 154(b) by 297 days.

(21) Appl. No.: 14/261,264

(22) Filed: Apr. 24, 2014

(65) Prior Publication Data

US 2015/0305761 A1    Oct. 29, 2015

(51) Int. Cl.
    *A61B 17/28*       (2006.01)
    *A61B 3/10*        (2006.01)
                (Continued)

(52) U.S. Cl.
    CPC .............. *A61B 17/28* (2013.01); *A61B 3/102* (2013.01); *A61B 17/30* (2013.01); *A61B 34/75* (2016.02);
                (Continued)

(58) Field of Classification Search
    CPC ......... A61B 17/28; A61B 17/00; A61B 17/30; A61B 34/75; A61B 2017/0025;
                (Continued)

(56) References Cited

U.S. PATENT DOCUMENTS 6,204,620 B1 * 3/2001 McGee ................. B25J 9/1679
                                               254/1
2012/0101508 A1   4/2012   Choi et al.
               (Continued)

FOREIGN PATENT DOCUMENTS

EP          2070487 A2    6/2009
WO   WO 2012012540 A2 * 1/2012 ............. A61B 17/00

OTHER PUBLICATIONS

Ansys Fluent, 30.2 Velocity Reporting Options, FLUENT 6.3 User's Guide, Sep. 20, 2006.*
(Continued)

*Primary Examiner* — Abby Lin
(74) *Attorney, Agent, or Firm* — Venable LLP; Henry J. Daley (57) ABSTRACT

A motion-compensated micro-forceps system, including a manually-operable micro-forceps assembly having a plurality of moveable grasping elements; a motor assembly operatively connected to the plurality of moveable grasping elements; an optical detection system having an optical fiber attached to the manually-operable micro-forceps assembly at a fixed axial distance relative to a distal-most end of the plurality of moveable grasping elements; and a motor controller configured to communicate with the optical detection system and the motor assembly to provide motion compensation of the plurality of moveable grasping elements of the manually-operable micro-forceps, wherein the optical detection system is configured to output a signal for the determination of a distance of the plurality of moveable grasping elements of the micro-forceps to a target during operation, and wherein the motor controller is configured to provide feedback control signals to the motor assembly for motion compensation for both hand tremor and for hand-action-induced motions.

16 Claims, 5 Drawing Sheets

(51) Int. Cl.
 A61B 17/30 (2006.01)
 A61B 34/00 (2016.01)
 A61B 17/29 (2006.01)
 A61B 90/00 (2016.01)
(52) U.S. Cl.
 CPC .............. A61B 34/70 (2016.02); A61B 34/76 (2016.02); A61B 2017/2918 (2013.01); A61B 2017/305 (2013.01); A61B 2090/3735 (2016.02)
(58) Field of Classification Search
 CPC ...... A61B 2017/305; A61B 2034/2055; A61B 3/102; A61B 5/0066; A61B 9/02054; G01B 9/02076; G01B 9/02091
 See application file for complete search history.

(56) References Cited

U.S. PATENT DOCUMENTS

| | | | |
|---|---|---|---|
| 2012/0133787 A1* | 5/2012 | Yamaguchi | H04N 5/2258 348/208.6 |
| 2013/0096574 A1 | 4/2013 | Kang et al. | |
| 2013/0123759 A1 | 5/2013 | Kang et al. | |
| 2013/0345719 A1 | 12/2013 | Donhowe et al. | |
| 2014/0078512 A1 | 3/2014 | Kang et al. | |

OTHER PUBLICATIONS

International Search Report of International Application No. PCT/US2015/026506, dated Jul. 13, 2015.
Ang et al., "Design and Implementation of Active Error Canceling in Hand-held Microsurgical Instrument," Proceedings of the 2001 IEEE/RSJ International Conference on the Intelligent Robots and Systems, Oct. 29-Nov. 3, 2001, pp. 1106-1111.
Beasley et al., "Kinematic Error Correction for Minimally Invasive Surgical Robots," Proceedings of the 2004 IEEE International Conference of Robotics & Automation, 2004, pp. 358-364.
Dario et al., "Smart Surgical Tools and Augmenting Devices," IEEE Transactions on Robotics and Automation, vol. 19, No. 5, 2003, pp. 782-792.
Du et al., "Robustness analysis of a smart surgical drill for cochleostomy," Int J Med Robotics Comput Assist Surg 2013: p. 119-126.
He et al., "Force sensing micro-forceps with integrated fiber Bragg grating for vitreoretinal surgery," Proc. SPIE 8218, 82180W-1~7 (2012).
Huang et al., "Motion-compensated hand-held common-path Fourier-domain optical coherence tomography probe for image-guided intervention," Biomed. Opt. Express 3(12), 3105-3118 (2012).
Hubschman et al., "'The Microhand': a new concept of micro-forceps for ocular robotic surgery," Nat. Eye 24, 364-367 (2010).
Ikuta et al., "Development of micro-active forceps for future microsurgery", Minimally Invasive Ther. Allied Technol. 10(4/5), 209-213 (2001).
Kang et al., "Common-path optical coherence tomography for biomedical imaging and sensing," J. Opt. Soc. Korea 14(1), 1-13 (2010).
Kang et al., "Endoscopic Functional Fourier Domain Common Path Optical Coherence Tomography for Microsurgery," IEEE J. of Sel. Top. Quantum Electron. 16(4), 781-792 (2010).
Kawai et al., "Development of exchangeable microforceps for a micromanipulator system," Adv. Robotics 15(3), 301-305 (2001).
Kuru et al., "Force Sensing Micro-forceps for Robot Assisted Retinal Surgery," in Proceedings of IEEE Conference on Engineering in Medicine and Biology Society (Institute of Electrical and Electronics Engineers, San Diego, 2012), pp. 1401-1404.
Riviere et al., "Robotic Compensation of Biological Motion to Enhance Surgical Accuracy," Proc. of the IEEE 94(9), 1705-1716 (2006).
Seiler et al., "Using Lie Group Symmetries for Fast Corrective Motion Planning," Algorithmic Foundations of Robotics IX, Springer Tracts in Advanced Robotics vol. 68, 2011, pp. 37-52.
Song et al., "Active tremor cancellation by a "smart" handheld vitreoretinal microsurgical tool using swept source optical coherence tomography," Opt. Express 20(21), 23412-23421 (2012).
Zhang et al., "A Surface Topology and Motion Compensation System for Microsurgery Guidance and Intervention based on Common-Path Optical Coherence Tomography," IEEE Trans. Biomed. Eng. 56(9), 2318-2321 (2009).

* cited by examiner

MOTION-COMPENSATED MICRO-FORCEPS SYSTEM AND METHOD

GOVERNMENT INTEREST

This invention was made with government support under 90046937 awarded by the National Institutes of Health and National Eye Institute. The government has certain rights in the invention.

TECHNICAL FIELD

The present invention relates to systems, methods and medical devices for use in guiding micro-forceps using fiber-optic common-path optical coherence tomography (CP-OCT).

BACKGROUND

Presently, highly skilled retinal surgeons complete basic microsurgical objectives by employing high levels of concentration, dexterity and fine motor control, bringing years of training and experience to bear on the defined motor task. Safely and efficiently performing retinal microsurgery requires accurate and precise tool tip control. Accuracy and precision can be facilitated by reducing physiological hand tremor that predominates in a frequency band of about 6-12 Hz, with on the order of 100 μm of motion that is neither directed nor intended. The peeling of micron scale membranes from the delicate retinal surface, without damaging its fragile neurons, is usually accomplished with unassisted freehand tools, such as, for example, a micro-forceps. Attempts to improve the micro-forceps have included, but not limited to, (1) built-in fiberscope and end-effectors to assist in retinal surgery tasks; (2) miniaturization and use of exchangeable micro-forceps as a part of micromanipulation system to assist in minimally invasive surgery; and (3) MEMS technology being applied to the development of micro-forceps for intraocular surgery. See D. C. Riviere, J. Gangloff, and M. Mathelin, "Robotic Compensation of Biological Motion to Enhance Surgical Accuracy," Proc. of the IEEE 94(9), 1705-1716 (2006); K. Ikuta, T. Kato and S. Nagata, "Development of micro-active forceps for future microsurgery", Minimally Invasive Ther. Allied Technol. 10(4/5), 209-213 (2001); and T. Kawai, K. Nishizawa, F. Tajima, K. Kan, M. Fujie, K. Takakura, S. Kobayashi, and T. Dohi, "Development of exchangeable microforceps for a micromanipulator system," Adv. Robotics 15(3), 301-305 (2001), which are herein incorporated by reference in their entirety.

Over the last decade, optical coherence tomography (OCT) has emerged as a dominant diagnostic imaging modality in clinical ophthalmology. See J-P Hubschman, J-L Bourges, W. Choi, A. Mozayan, A. Tsirbas, C-J Kim, and S-D Schwartz, "'The Microhand': a new concept of microforceps for ocular robotic surgery," Nat. Eye 24, 364-367 (2010), which is herein incorporated by reference in its entirety. Recently, a force sensing, fiber Bragg grating based micro-forceps to provide force feedback during vitreoretinal surgery has been presented. See X. He, M. A. Balicki, J. U. Kang, P. L. Gehlbach, J. T. Handa, R. H. Taylor, and I. I. Iordachita, "Force sensing micro-forceps with integrated fiber Bragg grating for vitreoretinal surgery," Proc. SPIE 8218, 82180W-1~7 (2012), which is herein incorporated by reference in its entirety. Nevertheless, its application as a potential sensor for intraoperative tool control is fairly new.

A microsurgical tool platform Smart Micromanipulation Aided Robotic-surgery Tool (SMART) has been presented for its ability to cancel a surgeon's physiological tremor and to stabilize a handheld imaging probe. See I. Kuru, B. Gonenc, M. Balicki, J. Handa, P. Gehlbach, R. H. Taylor, I. Iordachita, "Force Sensing Micro-forceps for Robot Assisted Retinal Surgery," in Proceedings of IEEE Conference on Engineering in Medicine and Biology Society (Institute of Electrical and Electronics Engineers, San Diego, 2012), pp. 1401-1404; K. Zhang, W. Wang, J. Han and J. U. Kang, "A Surface Topology and Motion Compensation System for Microsurgery Guidance and Intervention based on Common-Path Optical Coherence Tomography," IEEE Trans. Biomed. Eng. 56(9), 2318-2321 (2009); J. U. Kang, J. H. Han, X. Liu, K. Zhang, "Common-path optical coherence tomography for biomedical imaging and sensing," J. Opt. Soc. Korea 14(1), 1-13 (2010); J. U. Kang, J. H. Han, X. Liu, K. Zhang, C. G. Song, and P. Gehlbach, "Endoscopic Functional Fourier Domain Common Path Optical Coherence Tomography for Microsurgery," IEEE J. of Sel. Top. Quantum Electron. 16(4), 781-792 (2010); Y. Huang, X. Liu, C. Song and J. U. Kang, "Motion-compensated hand-held common-path Fourier-domain optical coherence tomography probe for image-guided intervention," Biomed. Opt. Express 3(12), 3105-3118 (2012), which are herein incorporated by reference in their entirety. SMART instruments utilize common path, swept source optical coherence tomography (CP SS-OCT) in a closed loop with a piezoelectric motor-based feedback control system. Active tremor reduction of the SMART instruments is achieved by positioning and by continuously and rapidly repositioning the tool tip at a defined constant offset distance from the sample surface by using the piezoelectric motor response to the distance sensing functions of the SS-OCT. The sensor response function of the tool prevents unintended tissue contact and damage, stabilizes tool tip tremor and allows steady positioning of the tool tip at previously unsustainable distances from the target tissue. However, this SMART platform has not been applied to the more complicated functions of micro-forceps.

What is needed are methods, systems and medical devices directed to micro-forceps that can assist in surgical precision and accuracy using OCT.

SUMMARY

In one embodiment, a motion-compensated micro-forceps system includes a manually-operable micro-forceps assembly that has a plurality of moveable grasping elements; a motor assembly operatively connected to the plurality of moveable grasping elements; an optical detection system comprising an optical fiber attached to the manually-operable micro-forceps assembly at a fixed axial distance relative to a distal-most end of the plurality of moveable grasping elements; and a motor controller configured to communicate with the optical detection system and the motor assembly to provide motion compensation of the plurality of moveable grasping elements of the manually-operable micro-forceps, wherein the optical detection system is configured to output a signal for the determination of a distance of the plurality of moveable grasping elements of the micro-forceps to a target during operation, and wherein the motor controller is configured to provide feedback control signals to the motor assembly for motion compensation for both hand tremor and for hand-action-induced motions.

In another embodiment, a method of performing motion compensation for a micromanipulation system may be provided that comprises detecting a distance of a distal-most end of the micromanipulation system to an object of interest; detecting an axial velocity of the distal-most end of the micromanipulation system to the object of interest; setting a safety barrier distance for the distal-most end of the micromanipulation system to the object of interest; and modifying the axial velocity proportional to a distance offset between the safety barrier distance and the distal-most end of the plurality of moveable grasping elements using feedback control with a motor controller and a motor system, wherein the modifying the axial velocity is adapted to provide motion compensation for both hand tremor and for hand-action-induced motions.

Additional features, advantages, and embodiments of the invention are set forth or apparent from consideration of the following detailed description, drawings and claims. Moreover, it is to be understood that both the foregoing summary of the invention and the following detailed description include examples and are intended to provide further explanation without limiting the scope of the invention as claimed.

DETAILED DESCRIPTION

Some embodiments of the current invention are discussed in detail below. In describing embodiments, specific terminology is employed for the sake of clarity. However, the invention is not intended to be limited to the specific terminology and examples selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated. All references cited in this specification are incorporated herein by reference.

The term "real-time" is intended to mean that the OCT images can be provided to the user during use of the OCT system. In other words, any noticeable time delay between detection and image display to a user is sufficiently short for the particular application at hand. In some cases, the time delay can be so short as to be unnoticeable by a user.

Figure 1:
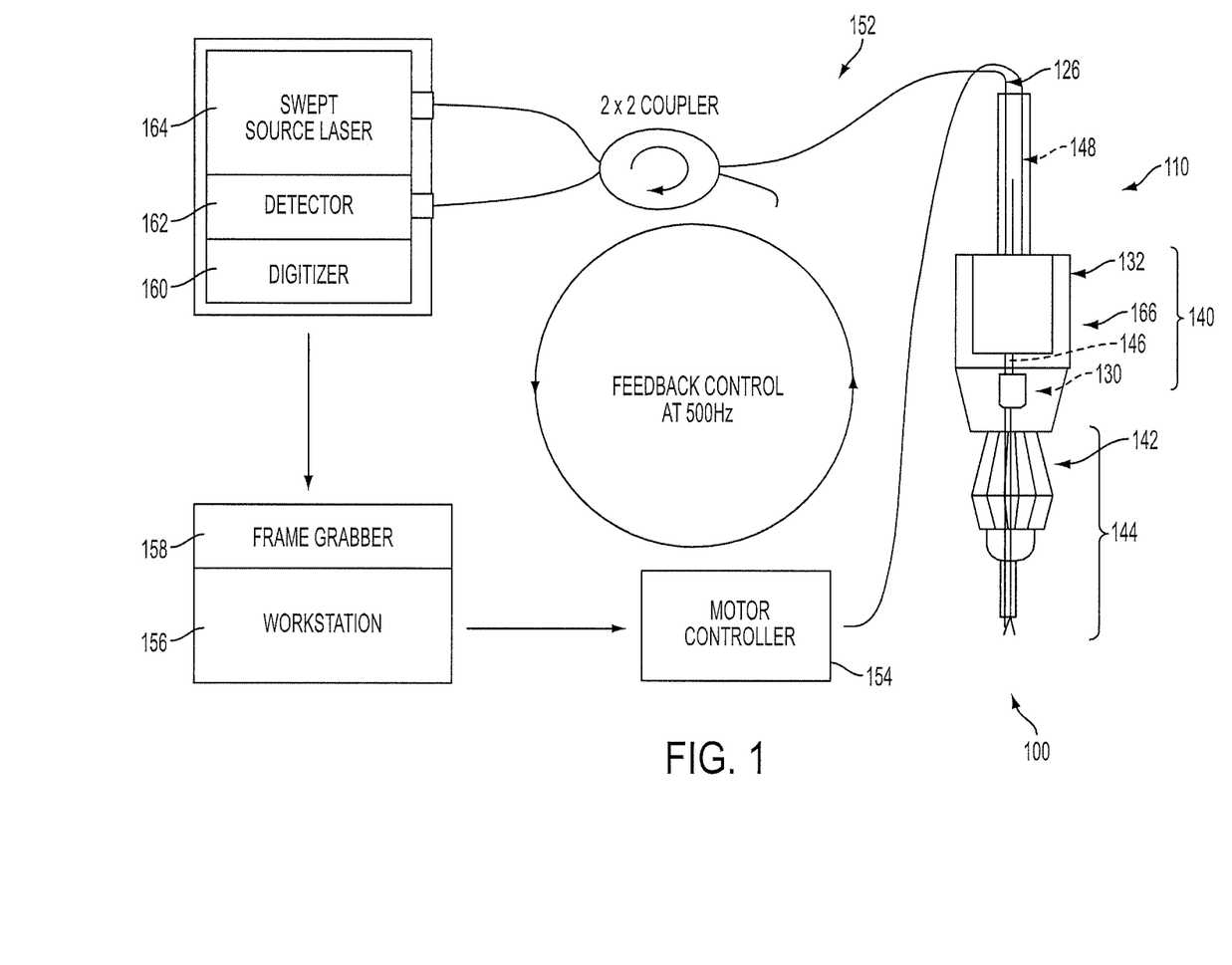
FIG. 1 illustrates a micro-forceps system configuration.

In FIG. 1, a motion-compensated micro-forceps system 100 includes a manually-operable micro-forceps assembly 144 that has a plurality of moveable grasping elements 134; a motor assembly 140 operatively connected to the plurality of moveable grasping elements 134; an optical detection system 152 comprising an optical fiber 126 attached to the manually-operable micro-forceps assembly 144 at a fixed axial distance relative to a distal-most end of the plurality of moveable grasping elements 134; and a motor controller 154 configured to communicate with the optical detection system 152 and the motor assembly 140 to provide motion compensation of the moveable grasping elements 134 of the manually-operable micro-forceps assembly 144, wherein the optical detection system 152 is configured to output a signal for the determination of a distance of the plurality of moveable grasping elements 144 of the micro-forceps to a target during operation, and wherein the motor controller 154 is configured to provide feedback control signals to the motor assembly 140 for motion compensation for both hand tremor and for hand-action-induced motions.

The micro-forceps 110 can include the micro-forceps assembly 144 having a plurality of moveable grasping elements 142. The moveable grasping elements 142 can be thin-walled plastic ribs that make up the body of the micro-forceps assembly 144. The micro-forceps 110 can include a motor assembly 140 that is operatively connected to the moveable grasping elements 142. The motor assembly 140 can have a drive rod 146, can comprise a motor 132, can have a speed of up to 15 mm/s, and can have a resolution of less than 1 nm. The micro-forceps 110 can include a tool handle 166 that can surround the motor assembly 140. Thus, the OCT sensor 126 can assess a tool tip motion relative to the target and compensate for unwanted and unintended tremor by using the motor 132 connected to the micro-forceps' tip. One example of such a piezoelectric motor is a LEGS-LL1011A PiezoMotor. The motor 132 can be a high speed piezoelectric motor and/or a PZT motor. The micro-stepping frequency from the motor controller 154 can be up to 125 kHz.

An optical detection system 152 can include the micro-forceps 110. The optical detection system 152 can be a common path OCT system, which can include a swept laser source 164. The optical detection system 152 can include a swept source (SS) OEM engine 164 (such as an AXSUN where $\lambda_0$=1060 nm, sweeping rate=100 kHz, 3 db axial resolution=8 μm, and scan range=3.7 mm in air), a 2×2 coupler 150, a photodetector 162 and a digitizer 160 with a sampling rate of up to 500 MSPS and 12 bit resolution. The optical detection system 152 can include an optical fiber 126 configured to be attached to the micro-forceps 110 at a fixed axial distance relative to a distal-most end of the moveable grasping elements 142. The swept source original equipment manufacturer (SS OEM) engine 164 can include a Camera Link DAQ Board to handle OCT signals such as the SD-OCT signal, which can be connected to a Camera Link frame grabber 158 that can be associated with the workstation 156.

The micro-forceps 110 can include an electrical wire 148 that is operable to connect with a motor controller 154. The micro-forceps system 100 can include the motor controller 154, which is configured to communicate with the optical detection system 152 and the motor assembly 140, so as to provide motion compensation of the plurality of moveable grasping elements 142 of the manually-operable micro-forceps assembly 144. The micro-forceps 110 can be configured such that the size and the shape of the micro-forceps 110 can be hand-operable.

The optical detection system 152 can be configured to output a signal for determining a distance of the moveable grasping elements 142 of the micro-forceps 110 to a target during operation. For example, a LabVIEW-based OCT signal processing and feedback control scheme can be used to update a closed-loop at 500 Hz through the workstation 156. In this way, the surgical micro-forceps' tip at a predetermined offset distance can be positioned and the distance during the grasping movement can be maintained independent of the surgeon and target motion. The motor controller 154 can be configured to provide feedback control signals to the motor assembly 140 for motion compensation for both hand tremor and for hand-action-induced motions. The motor compensation speed of 500 Hz is substantially higher than that required to compensate for a typical tremor frequency of 0-15 Hz. The proportional-integral-derivative (PID) feedback control is similar to that reported in previous SMART systems, such as C. Song, P. L. Gehlbach, and J. U. Kang, "Active tremor cancellation by a "smart" handheld vitreoretinal microsurgical tool using swept source optical coherence tomography," Opt. Express 20(21), 23412-23421 (2012), which is herein incorporated in its entirety by reference. The PID feedback control can include 1) surface detection of the target sample using an OCT signal; 2) activation of tremor compensation; and 3) action of micro-forceps grasping function.

In one embodiment, the micro-forceps 110 can be based on the CP SS-OCT operating at a center wavelength of 1060 nm and feedback control scheme at an update speed of 500 Hz. The micro-forceps system 100 can include a manually-operable micro-forceps 110 and a fiber-optic CP SS-OCT sensor 126, which is designed for precision distance sensing. The micro-forceps 110 can be, for example, an active surgical tool tip capable of high-speed precise axial motion to form the basis of a SMART tool platform. The SS-OCT system 100 and a PZT motor controller 154 can be connected to a workstation computer 156 having at least one processor, such as a Dell, T7500.

Figure 2A:
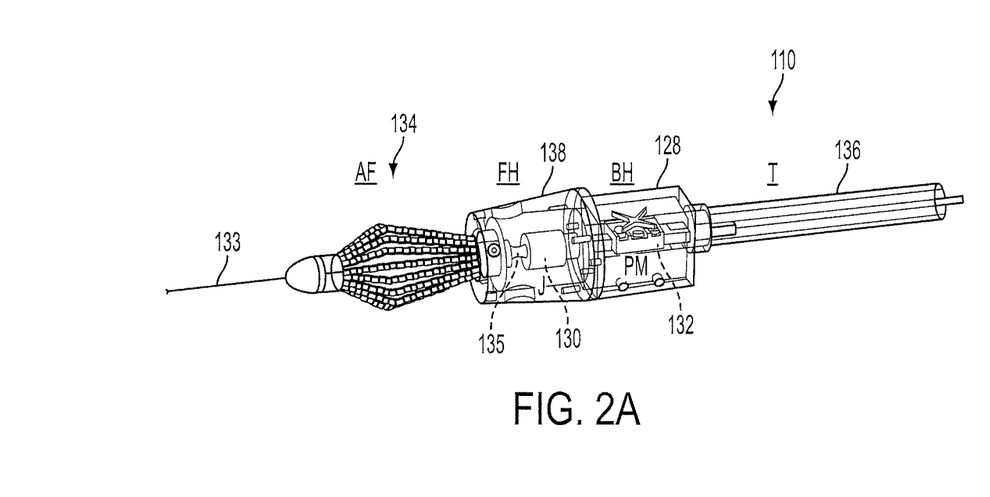
FIG. 2A shows a CAD rendering of a cross-sectional image of a micro-forceps assembly.
Figure 2B:
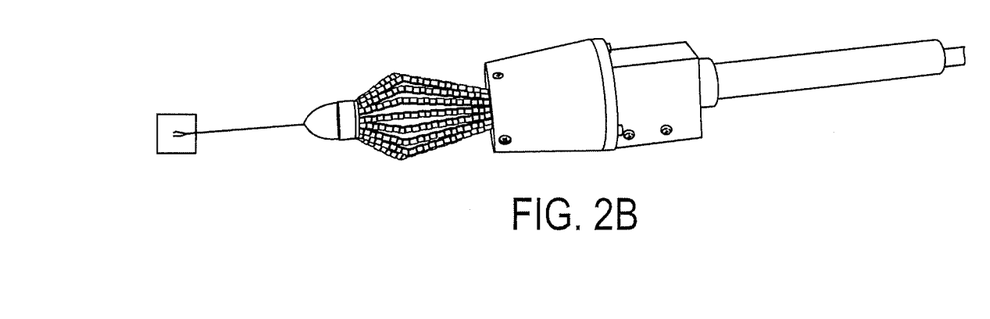
FIG. 2B shows an image of the implemented micro-forceps prototype.

FIG. 2A shows one embodiment of the micro-forceps system 100. FIG. 2A shows Alcon micro-forceps assembly 144, front holder 138, back holder 128, joint 130, tail 136, piezoelectric motor 132.

Figures 2C, 2D, 2E:
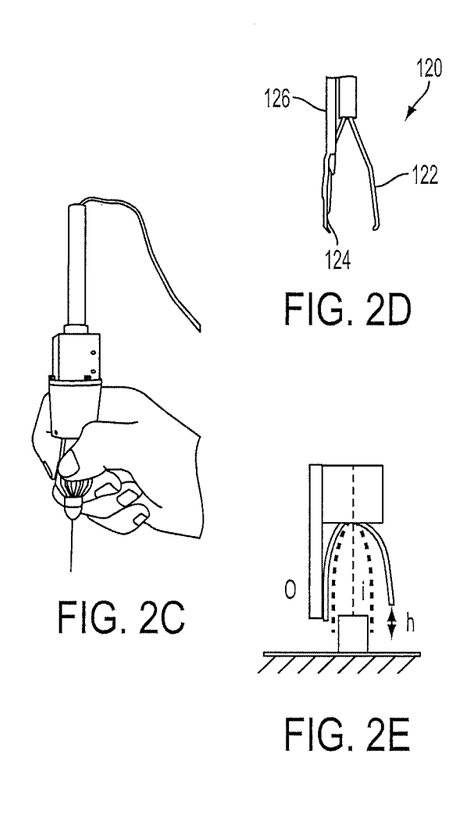
FIG. 2C shows a micro-forceps in use.
FIG. 2D shows a magnified view of optical fiber attached to a finger of the micro-forceps.
FIG. 2E shows an asymmetric configuration of two fingers.

The micro-forceps assembly 144 of the micro-forceps 110 is now explained according to one embodiment. FIG. 2D shows an enlarged view of the optical fiber 126 glued to one finger 124 of the micro-forceps assembly 144. In the micro-forceps assembly 144, the optical fiber 126 can be glued along an outside of the micro-forceps assembly 144, as shown as "o" in FIG. 2E, to avoid artifact signals generated by the tissue edge at the time of grasping. One embodiment of the micro-forceps assembly 144 is incorporated in a commercially available and highly customized reusable micro-forceps commonly used in vitreoretinal surgery manufactured by Alcon, Inc. In this embodiment, manual action can occur by compressing the thin-walled plastic ribs 142 comprising its body, an outer needle 133 of the Alcon micro-forceps then moves forward to engage the two finger tips 122, 124 of the micro-forceps assembly 144. An inner needle 135 inclusive of the forceps fingers 122, 124 can be carefully modified to move freely and to be connected to the drive rod of a PZT motor.

FIG. 2E shows the asymmetric configuration of two fingers, i and o: inside and outside of the fingers, h: height error during grasping, optical fiber 126, full line (open grasp), dotted line (closed grasp). The configuration of the micro-forceps fingers can be asymmetrically modified to reduce an inherent height error as "h" in FIG. 2E, which results from the movement arc of the fingers 124, 122. In this embodiment, the optical fiber 126 can be used as a high-speed distance sensor and can be simply attached to the relatively straight finger 124 of the micro-forceps 144 assembly. To engage both finger tips 124, 122 of the micro-forceps assembly 144, the relative position between the inner and the outer needle should be initialized prior to conducting a tremor compensation experiment. Even though the inner needle is capable of moving throughout the 3 mm effective OCT sensing range, the inner micro-forceps' "finger" can be stabilized while in SMART assisted mode to a movement range of 0.5 mm in order to allow safe manipulation.

Figure 3A:
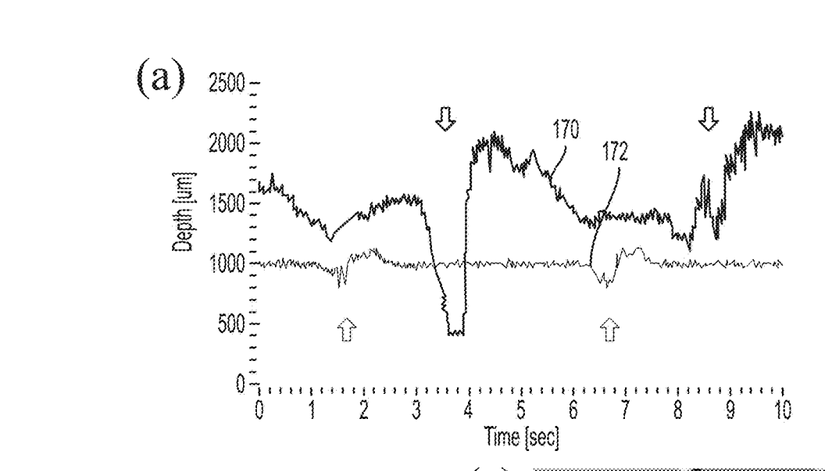
FIG. 3A shows two attempts to grasp starting from a defined offset height of 1000 μm for 10 seconds.
Figure 3B:
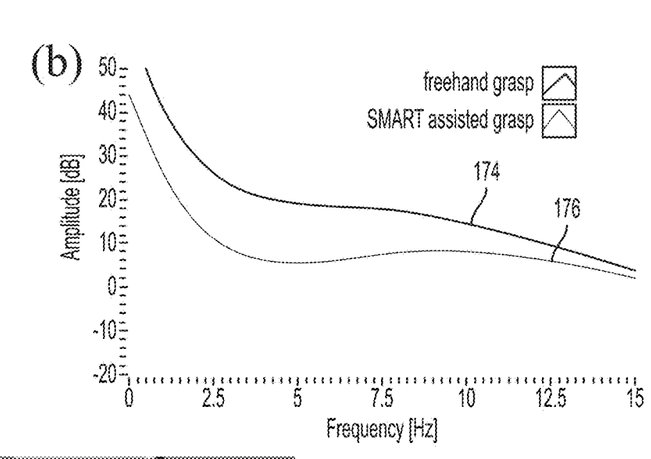
FIG. 3B shows the Fourier analysis of the two tip movement graphs.
Figure 3C:
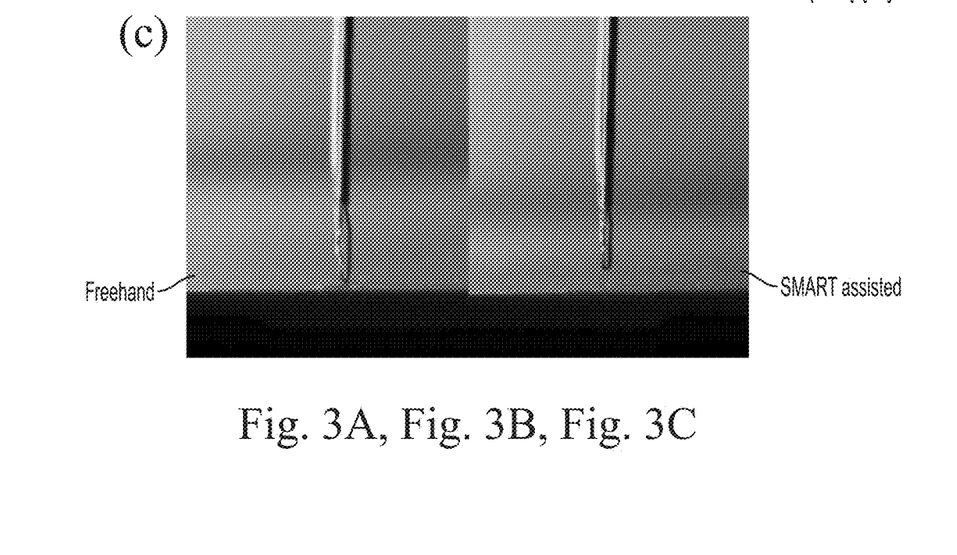
FIG. 3C shows freehand and assisted micro-forceps.

FIG. 3B shows an observable, quantifiable and significant reduction in the effect of the physiological tremor of around 6-12 Hz at the tool tip. In FIG. 3A, comparison is shown of tool tip position relative to the target surface during freehand grasp lines 170, 174 and SMART assisted grasp lines 172, 176 using a dry phantom (white paper). Also shown is a decrease of the low frequency band, on the order of 0-5 Hz that results in large amplitude instrument position drift. The micro-forceps system, enhanced with feedback control for real-time distance tracking, can effectively cancel unintended instrument drift. Thus, the micro-forceps 110 according to FIGS. 3A and 3B can be operative at tissue offset positions of up to a 3 mm effective OCT sensing distance from the target surface.

FIG. 3A shows 10 seconds of representative data captured during two attempts at freehand grasp line 170, which is compared to two attempts to grasp with the instrument assisted by tremor compensation line 172. FIG. 3A demonstrates the difference in tool tip stability both when maintaining the offset position and during the grasping motion of the micro-forceps 110. In the case of freehand grasp, tool tip motion can be on the order of 1000 μm directed towards the target surface. When assisted by tremor compensation, tool tip motion directed towards the target surface is generally less than 350 μm.

FIG. 3B shows averaged graphs of the Fourier analyses of up to 15 Hz from 5 data sets, with 20th order polynomial least-square fitting. The Fourier transformed amplitude of SMART assisted grasp data line 176 is less than that of freehand grasp data line 174. While both the unassisted and assisted grasping motions direct the tool tip towards the target, the amplitude reduction between the two Fourier transform data sets is relatively larger in the low frequency band (0-5 Hz) than in the high frequency band (10-15 Hz), as seen from FIG. 3B.

Figure 4A:
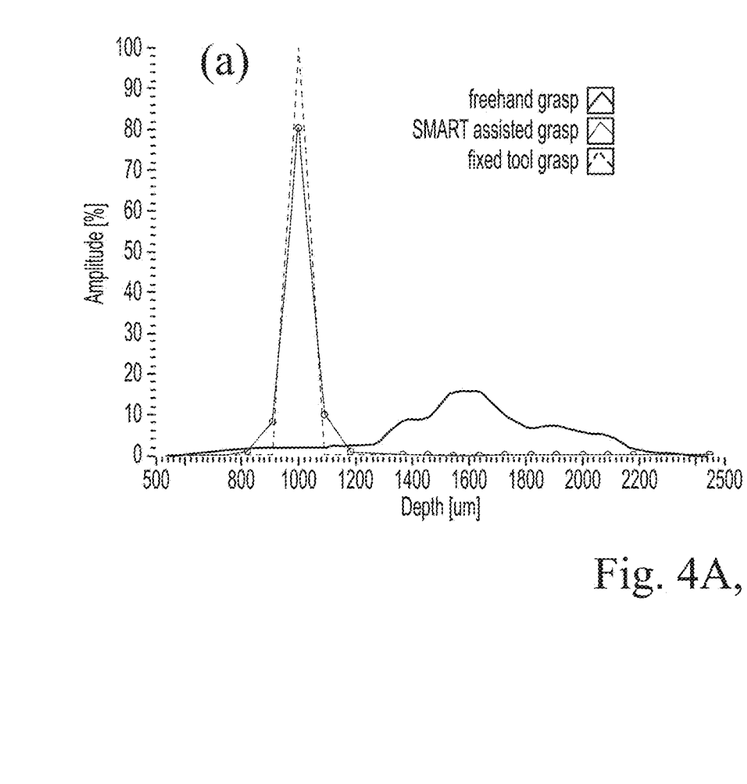
FIGS. 4A and 4B illustrate the grasp performance of the micro-forceps using two different parameters: grasp type and grasp time.
Figure 4B:
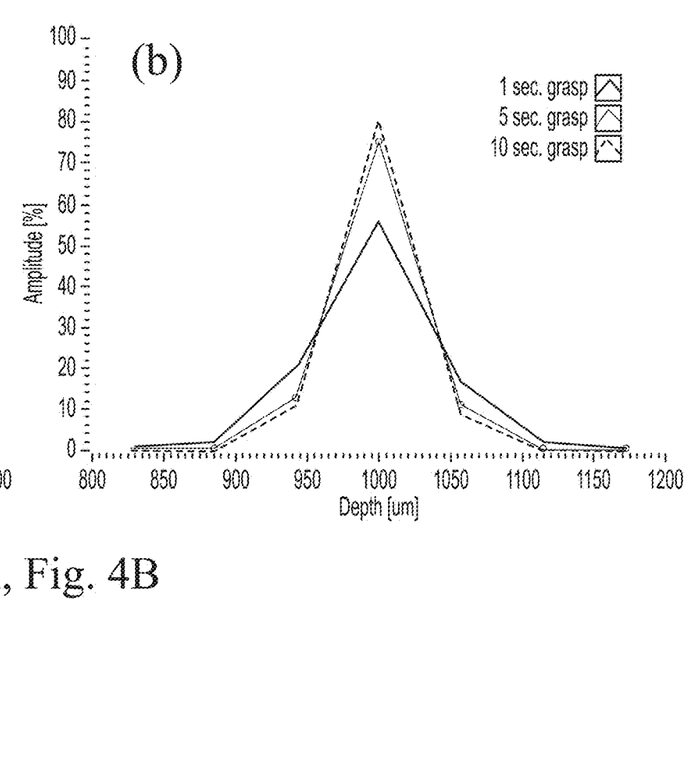

FIGS. 4A and 4B show a height histogram and RMSE of micro-forceps 110 in terms of grasp mode and grasp duration. The intrinsic grasp error of the micro-forceps without any tremor can be measured with tremor compensation on after firmly attaching it to a rigid body (tool position fixed). FIG. 4A shows height data analysis of the freehand, SMART assisted and in fixed position (two grasps for 10 seconds and one during 1 second) averaged from 5 data sets. FIG. 4A shows histograms of the Root Mean Square Error (RMSE) of grasping under the three different experimental conditions (freehand, SMART assisted, and fixed tool position with compensation on). This histogram graphs represent averaged data from 5 data sets. The narrow histogram in the SMART assisted grasp data supports the premise of improved tip control as compared to freehand use. The tool tip position of freehand grasp is by comparison highly variable in all ranges, particularly near 1600 μm. Freehand grasp may be inherently more difficult from an offset distance of 1000 μm.

FIG. 4B shows height comparison according to three different durations of SMART assisted grasp, which are averaged from 10 data sets; 1 second and 5 second grasps indicate sustained grasping every 5 seconds; 10 second grasp indicates that the grasp was sustained over 10 seconds. FIG. 4B shows an evaluation of SMART assisted grasping performance with time constraints. By increasing the time duration from 1 second to 5 seconds for grasp, the RMSE of the action can be decreased. Increasing the time for grasp up to 10 seconds did not substantially further reduce the RMSE.

The optical detection system 152 can be configured to output a signal for determining an axial velocity of the manually-operable micro-forceps 110 relative to an object of interest. The motor controller 154 can be configured to provide feedback control signals to the motor assembly 140 to compensate for hand-action-induced motions using the axial velocity determined from the optical detection system 152. The motor controller 154 can also be configured to provide feedback control signals to the motor assembly 140 based an algorithm that sets a safety barrier distance and modifies the axial velocity proportional to a distance offset between the safety barrier distance and the distal-most ends of the moveable grasping elements.

The algorithm can modify the axial velocity to decrease as the distance offset decreases and to become zero when the distance offset becomes zero. The algorithm can decrease modification of the axial velocity as a distance from the distance offset increases and allows resetting a registration position of the moveable grasping elements.

Figure 5A:
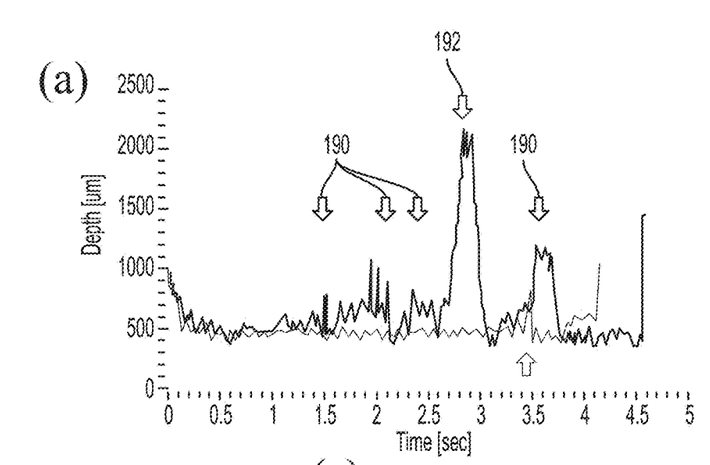
FIGS. 5A and 5B show the corresponding height signals and the Fourier analysis for both freehand and assisted peeling tests, respectively.
Figure 5B:
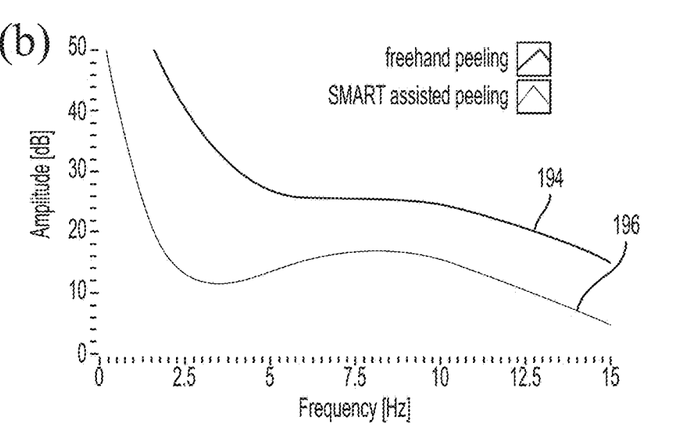
Figure 5C:
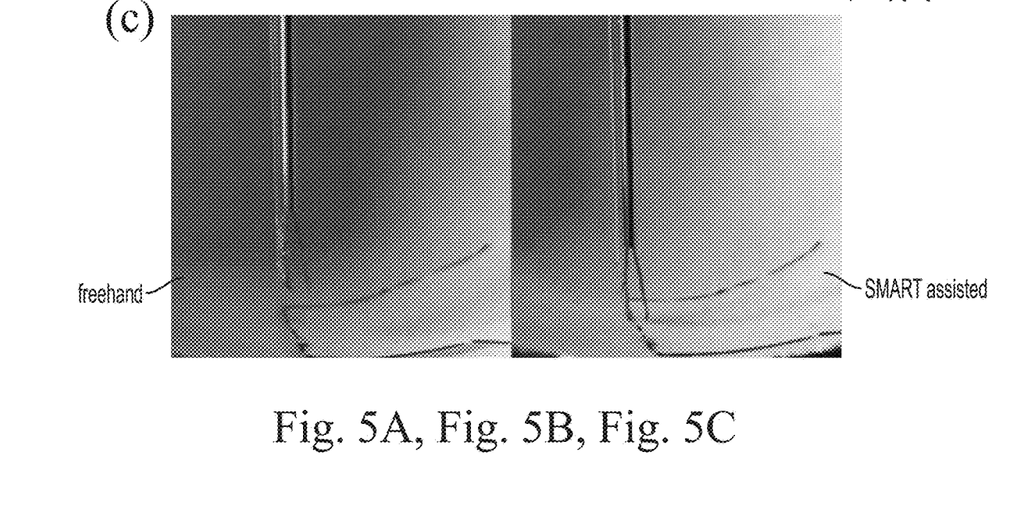
FIG. 5C shows freehand and assisted micro-forceps.

FIG. 5 shows a comparison of freehand peeling line 178 and SMART assisted peeling line 180 on an egg shell. Enhanced precision in micro-forceps peeling assisted by tremor compensation can also be demonstrated in a biological tissue model, thereby further validating its potential as a practical microsurgical device, as shown in FIG. 5. During peeling biological membranes (the inner and outer membrane of an egg shell), the SMART micro-forceps 110 can diminish hand tremor but also enable the user to precisely place the tool tip at a distance suitable for grasping and peeling. To assess micro-forceps peeling, a tough inner membrane can be incised prior to grasping. Then, a black ink may be applied to the edge of the membrane to clarify the membrane boundaries.

FIG. 5A shows continuous attempts to peel the membrane at a defined offset height of 500 μm. Each arrow 190 indicates the moment of a grasp and arrow 192 indicates a next attempt. FIG. 5B shows the Fourier analysis of two height signals, freehand peeling 194 and SMART-assisted peeling 196. Line 195 represents a freehand peeling whereas line 197 represents SMART assisted peeling.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

We claim:

1. A motion-compensated micro-forceps system, comprising:
    a manually-operable micro-forceps assembly comprising a plurality of moveable grasping elements;
    a motor assembly operatively connected to the plurality of moveable grasping elements;
    an optical detection system comprising an optical fiber attached to the manually-operable micro-forceps assembly at a fixed axial distance relative to a distal-most end of the plurality of moveable grasping elements; and
    a motor controller configured to communicate with the optical detection system and the motor assembly to provide motion compensation of the plurality of moveable grasping elements of the manually-operable micro-forceps assembly,
    wherein the optical detection system is configured to output a signal for the determination of a distance of the plurality of moveable grasping elements of the micro-forceps assembly to a target during operation, and
    wherein the motor controller is configured to provide feedback control signals to the motor assembly for motion compensation for both hand tremor and for a micro-forceps motion during grasping motions of the micro-forceps assembly, the grasping motions of the micro-forceps assembly being distinct from the hand tremor.

2. The motion-compensated micro-forceps system according to claim 1, wherein the optical detection system is further configured to determine an axial velocity and acceleration of the manually-operable micro-forceps assembly relative to an object of interest, and
    wherein the motor controller is further configured to provide feedback control signals to the motor assembly to compensate for predicted hand-action-induced motions using the axial velocity and acceleration determined from the optical detection system.

3. The motion-compensated micro-forceps system according to claim 2, wherein the motor controller is further configured to provide feedback control signals to the motor assembly based on an algorithm that sets a safety barrier distance and modifies the axial velocity proportional to a distance offset between the safety barrier distance and the distal-most ends of the plurality of moveable grasping elements.

4. The motion-compensated micro-forceps system according to claim 3, wherein the algorithm modifies the axial velocity to decrease as the distance offset decreases and to become zero when the distance offset becomes zero.

5. The motion-compensated micro-forceps system according to claim 1, wherein the optical detection system is a common path optical coherence tomography system.

6. The motion-compensated micro-forceps system according to claim 5, wherein the common path optical coherence tomography system comprises a swept laser source.

7. The motion-compensated micro-forceps system according to claim 1, wherein the motion-compensated micro-forceps system has a size and shape to be hand-operable during use.

8. The motion-compensated micro-forceps system according to claim 1, wherein the micro-forceps assembly comprises fingers and wherein the micro-forceps assembly is modified to reduce a height difference between the micro-forceps assembly and a surface, wherein the height difference is a result of at least one of the fingers of the micro-forceps assembly moving between an open position and a closed position of the micro-forceps assembly.

9. A method of performing motion compensation for a micromanipulation system, comprising:
- detecting a distance of a distal-most end of the micromanipulation system to an object of interest;
- detecting an axial velocity of the distal-most end of the micromanipulation system to the object of interest;
- setting a safety barrier distance for the distal-most end of the micromanipulation system to the object of interest; and
- modifying the axial velocity proportional to a distance offset between the safety barrier distance and the distal-most end of the micromanipulation system using feedback control with a motor controller and a motor system,
- wherein the modifying the axial velocity is adapted to provide motion compensation for both hand tremor and for the micromanipulation system motion during grasping motions of the micromanipulation system, the grasping motions of the micromanipulation system being distinct from the hand tremor;
- wherein the micromanipulation system comprises a hand-operable, motion-compensated micro-forceps system.

10. The method of performing motion compensation for a micromanipulation system according to claim 9, wherein the modifying the axial velocity decreases the axial velocity as the distance offset decreases to become zero when the distance offset becomes zero.

11. The method of performing motion compensation for a micromanipulation system according to claim 9, wherein detecting said distance of said distal-most end of the micromanipulation system to said object of interest is detecting said distance of said distal-most end of the micromanipulation system.

12. The method of performing motion compensation for a micromanipulation system according to claim 11, wherein detecting said distance of said distal-most end of the micromanipulation system to said object of interest is detecting said distance of said distal-most end of the hand-operable, motion-compensated micro-forceps system that comprises:
- a manually-operable micro-forceps assembly comprising a plurality of moveable grasping elements;
- a motor assembly operatively connected to the plurality of moveable grasping elements;
- an optical detection system comprising an optical fiber attached to the manually-operable micro-forceps assembly at a fixed axial distance relative to a distal-most end of the plurality of moveable grasping elements; and
- a motor controller configured to communicate with the optical detection system and the motor assembly to provide motion compensation of the plurality of moveable grasping elements of the manually-operable micro-forceps assembly .

13. The method of performing motion compensation for a micromanipulation system according to claim 12, further comprising outputting a signal from the optical detection system for the determination of the axial velocity of the manually-operable micro-forceps assembly relative to the object of interest, and
- providing feedback control signals from the motor controller to the motor assembly to compensate for hand-action-induced motions using the axial velocity determined from the optical detection system.

14. The method of performing motion compensation for a micromanipulation system according to claim 12, wherein detecting said distance of said distal-most end of the micromanipulation system to said object of interest is detecting said distance of said distal-most end of the hand-operable, motion-compensated micro-forceps system that comprises a common path optical coherence tomography system.

15. The method of performing motion compensation for a micromanipulation system according to claim 14, wherein detecting said distance of said distal-most end of the micromanipulation system to said object of interest is detecting said distance of said distal-most end of the hand-operable, motion-compensated micro-forceps system that comprises the common path optical coherence tomography system comprises a swept laser source.

16. The method of performing motion compensation for a micromanipulation system according to claim 9, wherein the micro-forceps system comprises fingers, the method further comprising:
- modifying a configuration of the fingers of the micro-forceps system to reduce a height difference between the micro-forceps system and a surface, wherein the height difference is a result of at least one of the fingers moving between an open position and a closed position of the micro-forceps system.

* * * * *

UNITED STATES PATENT AND TRADEMARK OFFICE
CERTIFICATE OF CORRECTION

PATENT NO. : 9,872,692 B2
APPLICATION NO. : 14/261264
DATED : January 23, 2018
INVENTOR(S) : Jin U. Kang and Peter L. Gehlbach Page 1 of 1

It is certified that error appears in the above-identified patent and that said Letters Patent is hereby corrected as shown below:

Column 1, Lines 4-9 should read:
STATEMENT OF GOVERNMENTAL INTEREST
This invention was made with government support under grant number 9046937, awarded by the National Science Foundation. The government has certain rights in the invention.

Signed and Sealed this
Twentieth Day of November, 2018

Andrei Iancu
*Director of the United States Patent and Trademark Office*